United States Patent [19]

Beaver

[11] Patent Number: 4,966,613
[45] Date of Patent: Oct. 30, 1990

[54] METHOD OF PRODUCING EFFECTIVE POROUS GLASS SHAPES

[75] Inventor: Richard P. Beaver, Library, Pa.

[73] Assignee: PPG Industries, Inc., Pittsburgh, Pa.

[21] Appl. No.: 677,106

[22] Filed: Nov. 30, 1984

[51] Int. Cl.$^5$ .................. C03B 37/075; C03B 19/10; C03C 15/00

[52] U.S. Cl. .................. 65/2; 65/21.4; 65/31

[58] Field of Search .............. 65/18.1, 21.4, 30.1, 65/30.13, 31, 33, 2, 3.15

[56] References Cited

U.S. PATENT DOCUMENTS

| | | | |
|---|---|---|---|
| 2,491,761 | 12/1949 | Parker et al. | 428/228 |
| 2,494,259 | 1/1950 | Nordberg | 501/35 |
| 2,500,092 | 3/1950 | Parker et al. | 156/663 |
| 2,635,390 | 4/1953 | Parker | 65/31 |
| 2,843,461 | 7/1958 | Labino | 156/663 |
| 2,861,351 | 11/1958 | Smith | 34/7 |
| 3,231,540 | 1/1966 | Vanderbilt | 260/41.5 |
| 3,375,155 | 3/1968 | Adams | 161/93 |
| 3,549,524 | 12/1970 | Haller | 210/31 |
| 3,650,721 | 3/1972 | Hammel et al. | 65/31 |
| 3,687,850 | 8/1972 | Gagin | 252/62 |
| 3,762,897 | 10/1978 | Johnson | 65/31 |
| 4,042,359 | 8/1977 | Schnabel et al. | 65/2 |
| 4,086,074 | 4/1978 | Minot et al. | 65/31 |
| 4,244,721 | 1/1981 | Gupta et al. | 65/31 |
| 4,319,905 | 3/1982 | Macedo et al. | 65/31 |

*Primary Examiner*—Kenneth M. Schor
*Attorney, Agent, or Firm*—Kenneth J. Stachel

[57] ABSTRACT

Porous glass shapes with effective pores are produced by a method which also reduces the frequency of breakage of the glass shapes. The method includes: producing a plurality of the glass shapes, depositing a fluid chemical treatment with one or more carbonaceous materials on a substantial portion of the surfaces of the glass shapes, heat treating the glass shapes to phase separate components of the glass, leaching the phase separated glass shapes to remove leachable components to produce pores in the glass shapes, and removing any residual carbonaceous material. The various forms of glass shapes include particles, platelets, flakes, beads, fibers both solid and hollow, tubes and capillaries, which are essentially free of carbonaceous material.

18 Claims, 2 Drawing Sheets

METHOD OF PRODUCING EFFECTIVE POROUS GLASS SHAPES

The present invention is directed to a method of producing distinct, porous silica-rich glass shapes like particles, flakes, beads, plates, tubes, capillaries, fibers and hollow fibers having effective pores, and the so-produced porous silica-rich glass shapes.

Numerous methods exist in the art for producing pores in glass where the exact method depends upon the exact composition of the glass. Glass beads and fibers and the like have been treated variously with heat treatments for phase separation of phase separable glass followed by water and/or acid leaching, or merely with acid leaching or with leaching with acids and/or alkali material to produce pores in the glass. For example, glass beads made from an the alkali metal borosilicate ternary glass system have been heat treated to phase separate the leachable materials from the nonleachable silica and acid treated to remove the phase separated leachable materials.

Porous glasses have been investigated for application in ultrafiltration, reverse osmosis, gaseous separations, gaseous liquid separations, liquid liquid separations, as catalyst supports and in the case of porous glass beads for enzyme and microbe immobilization.

The most common method of producing porous glasses appears to be formulating the glass shapes from alkali metal borosilicate glass composition with subsequent heat treatment for phase separation and acid leaching of the phase separated boron from the unleachable silica. In addition, this method is also used for producing high silica containing compositions having improved thermal stability. The distinct glass shapes having a large quantity of phase separable and leachable boron or boron-like materials, can result in nonuniform porous glass shapes with concomitant production of broken shapes or shape disruptions other than pores in subsequent leaching steps. Consequently, the final porous glass shape may not have the same shape as the starting article and/or may have reduced dimensions or distorted shapes.

It is an object of the present invention to provide a method of producing a plurality of distinct porous glass shapes from distinct heat treatable, phase separable glass compositions, where the shapes have more uniformity and effective pores, and where damage to the shapes is minimized.

It is a further object of the present invention to provide distinct porous glass shapes having more uniform shapes, effective pores and reduced shape damage or disruptions other than pores.

SUMMARY OF THE INVENTION

The present invention accomplishes the aforementioned objects and other objects gleaned from the following disclosure by providing a method of producing distinct porous, silica-rich glass shapes with good uniformity of the shapes and with effective pores through utilization of heat treatable, phase separable glass shapes and by providing the porous silica-rich shapes.

The method involves: forming the distinct glass shapes or their glassy precursors having at least a phase separable alkali metal borosilicate composition, treating the glass shapes or precursors with a fluid carbon-containing chemical material to provide the shapes with carbonaceous deposits, heat treating the glass shapes to phase separate a borate-rich phase and a silica-rich phase in the glass shapes, leaching a substantial amount of the borate-rich phase from the shapes to form porous silica-rich glass shapes, oxidizing at least a substantial amount of any remaining carbon on the porous silica-rich glass shapes to produce effective porous shapes while substantially maintaining the shape of the material prior to heat treating. The glass shapes that are formed can be those such as filaments, strands, capillaries, tubes, beads, platelets, flakes or particles, where the shapes are formed from shapable glass forming batch that yield phase separable glass compositions. The porous silica-rich shapes have a silica content of at least around 75 weight percent of the porous shape along with any inorganic metal oxide glass modifiers. In addition a minor amount of carbon may be present in the porous shape which has a pore volume in the range of greater than around 0.5 to around 1.5 cc/gm.

DETAILED DESCRIPTION OF THE INVENTION

Figure 1:
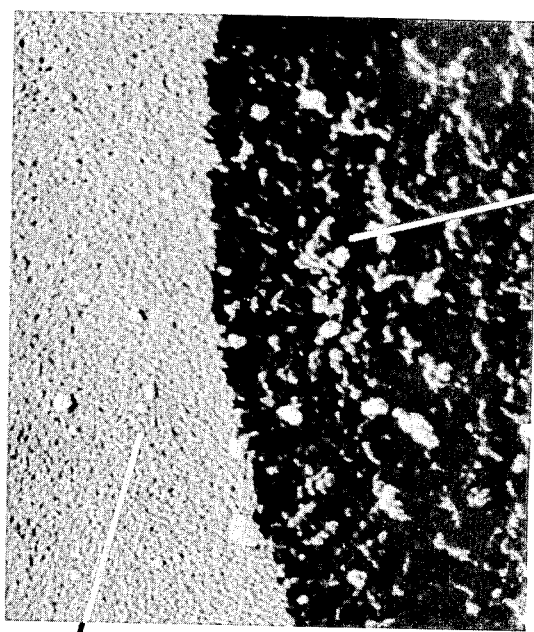
FIG. 1 is a photograph of a treated porous silica-rich glass shape of the present invention from a scanning electron microscope where the shape was magnified 12,000 times.

For better understanding of the following disclosure and claims the term "boron-containing materials" refers to boron, boron oxide, boron anhydride and alkali metal borates.

The yield and effectiveness of porous silica-rich shapes produced from leaching heat treated, phase separated glass shapes can be adversely affected by shape distortion, damage, and breakage during production. In heat treating, a plurality of distinct glass shapes that have a relatively high quantity of boron-oxide or other boron-containing materials or other inorganic oxides that reduce the softening point of the glass shapes, the distinct shapes become tack bonded at various contact points of the shapes. In subsequent water, acid and/or alkali leaching steps, the tack bonded contact points can result in nicks, distortions and/or breakage of the porous glass shapes.

It is believed without limiting the invention that the heat softened, phase separated components of the glass shapes that are responsible for the lower softening and/or melting points of the glass shapes cause the tack bonding of the heat treated glass shapes. During heat treatment, these softening components in shapes contacting one another can become fused or tack bonded at the point of contact. The tack bonding problem is solved by the present invention which provides a carbonaceous material present on the glass shapes during the heat treatment. But, it has been further discovered that if any carbonaceous material or its residue is left after heat treatment and leaching, the silica-rich glass shapes must be subjected to a carbon oxidation step to achieve effective pores in the porous silica-rich glass shapes.

The porous glass shapes of the present invention are prepared from shapable glass forming batch compositions which yield shaped glasses that are phase separable, when heat treated, and that are leachable after phase separation. These compositions are known to those skilled in the art as being in the alkali metal borosilicate ternary system. These compositions have leachable components such as boron containing materials and/or alkali metal oxides like sodium oxide, potassium oxide and lithium oxide in the glass shapes. With the presence of the boron-containing material especially boron oxide along with alkali metal oxides in the glass composition, the glass shapes have a reduced melting point and are readily formed from the batch composition. The batch composition is formulated to result in the glass shapes having essentially two groups of components upon phase separation. Typical batch material known to those skilled in the art can be used and calculated by known methods to produce the glass compositions with essentially two groups of components, a borate-rich group and a silica-rich group along with any aluminum oxide, other glass forming ingredients, fluxes, fining agents, alkali metal carbonates and aluminates. These included materials, if present, are present in amounts which do not adversely affect phase separation or leaching. Typical fining agents include sulfates, halides, ammonium salts, nitrates, peroxides, chlorates, $Sb_2O_3$ and the like. In the composition of the pore generating glass shape, the borate-rich group, includes the one or more boron-containing materials, the alkali metal oxides, possibly some aluminum oxide and any alkaline earth metal oxides. The silica-rich group has the siliceous material such as silica and oxides of glass modifiers like aluminum, zirconium, titanium and the like.

Generally, phase separable glass compositions resulting from the shapable batch composition have boron-containing materials in concentrations of greater than around 5 weight percent and preferably greater than 20 weight percent and most preferably greater than 40 weight percent but less than around 60 weight percent of the glass composition. The alkali metal oxide can be in the range from around 4 weight percent upwards of 20 weight percent as in a water glass. The silica forms the insoluble phase, when the glass is phase separated, and it is the principal component of the glass skeleton in the resultant porous glass shape of the present invention. The amount of siliceous material should not be less than around 25 and preferably not less than 30 weight percent of the total glass composition. Generally, the siliceous material is less than around 85, preferably less than around 70 weight percent of the total glass composition. The amounts of the other components in the silica-rich group can be the art recognized amounts of these materials or leachable glass compositions. The formulation of the glass forming batch results in glass shapes, wherein pores can be generated, by heat treating and water and/or acid leaching, and with or without alkali leaching or acid leaching with hydrofluoric or phosphoric acids to yield a pore volume in the range of about 0.5 to about 1.5 and preferably about 0.8 to about 1.2 cc/gm, and most preferably about 0.8 to about 1 cc/gm.

The glass batch compositions are melted according to methods well known in the industry. Ordinarily, powdered raw materials such as those containing sand, boric oxide, alkali metal oxides, and optionally aluminum materials are batched and mixed and melted together. While it is preferred that the raw materials be present in forms which, when mixed and heated, most readily fuse to form a melt, the oxides may be present either in the free state or in the form of other suitable components. Examples of suitable components are alkali metal carbonates, borates and aluminates.

A particularly useful heat treatable glass for phase separation formed from shapable batch composition has silica at 30 to 50 percent by weight, boric oxide at 40 to 55 percent by weight, alkali metal oxide at 5 to 15 percent by weight, and aluminum oxide from 0 to 4 weight percent. Nonexclusive examples of phase separable, borosilicate glasses are described in U.S. Pat. Nos. 2,106,744; 2,215,039 and 2,221,709 and 2,286,275; 3,972,720; 3,843,341 and 3,923,688, all of which are hereby incorporated by reference. The most preferred glass composition contains boric oxide at 54 weight percent, sodium oxide at 8.0 weight percent and silica at 38 weight percent.

The various glass shapes or articles can be formed by any method known to those skilled in the art. Glass beads can be formed as taught in U.S. Pat. Nos. 3,630,700; 3,650,721; 3,793,061; 3,834,911; 3,843,431; 3,923,533; 3,923,688; 3,972,720; and 3,972,721, all hereby incorporated by reference or any other art recognized method of forming glass beads. In the method of preparing solid or hollow fibers, strands, capillaries and tubes, the shapable glass compositions are the attenuatable glass compositions and for the fibers they are the fiberizable compositions. These attenuated shapes can be formed by gaseous blown flame, or centrifugal or mechanical attenuation of the fibers, capillaries or tubes, or any other procedures known by those skilled in the art. Also, the fibers can be formed as hollow fibers as described in U.S. Pat. Nos. 3,268,313; 3,421,873; and 3,510,393, all of which are hereby incorporated by reference. The capillaries or tubes can be formed by any method known in the art; for instance, by the method shown in U.S. Pat. No. 4,042,359, hereby incorporated by reference.

One particular, non-exclusive method of forming glass shapes is that for forming fibers. A fiberizable glass batch composition is melted in a glass batch melting furnace at the requisite temperature and time or the particular glass composition. Generally, the temperature range is from about 2000° F. (1093° C.) to about 3000° F. (1649° C.) for around 1 to about 6 hours or longer. The molten glass is attenuated through bushing tips located at the bottom of the heated glass fiber forming bushing which contains the molten glass. The fibers may be cooled with air and/or water by pre-pad spray jets as they leave the bushing depending on the type of fiber being produced. For the high boron content fibers, it is preferred not to contact the fibers with water to assist in cooling the fibers. The diameter of the fibers formed from the bushings can vary rom the submicron range to a diameter for capillaries or tubes. For the fibers, the diameters range from about 1 micron to less than around 150 microns so the fibers can be wound into a cylindrical package. The lengths of the fibers, strands, capillaries and tubes can be continuous in that their lengths can be cut into any desired lengths, which are capable of being processed further in heat treatment and leaching. Generally, the lengths range from about 1/32 of an inch (0.03 inch 0.08 cm) for the chopped fibers to many feet for tubular shapes.

The formed, distinct glass shapes or their glassy precursors are treated with a fluid chemical treatment having a carbon-containing or carbonaceous material which is deposited on a substantial portion of the surfaces of the distinct glass shapes or their glassy precursors. By glassy precursors, it is meant that in the case of flakes, platelets or particles, these materials may be formed by downsizing or comminuting larger formed glass shapes. In this case, the larger formed glass shapes may be chemically treated before formation of the flakes, platelets or particles by ambient temperature methods known to those skilled in the art. In order for the fluid chemical treatment with carbonaceous material to be deposited on the distinct glass shapes or their glassy precursors, the glass shapes or precursors are cooled from their forming temperatures. The fluid chemical treatment can be an aqueous or organic solution gel or foam, although aqueous solutions are preferred to avoid any fire hazard because of the proximity of chemical treatment of the glass shapes or precursors to the molten temperatures of their formation. Hereinafter and in the claims the term "glass shapes" shall include formation by "glassy precursors".

The fluid chemical treatment has one or more carbonaceous material that are soluble, dispersible or emulsifiable in water or organic solvents or in gels or foams. Examples of the carbonaceous materials include any of the fluidizable chemical treating compounds known to those skilled in the art for treating glasses such as glass fibers. Nonexclusive examples include nonionic, cationic or anionic glass fiber lubricants including alkyl imidazoline derivatives which include compounds of the class N-alkyl N-amidoalkyl imidazolines which may be formed by causing fatty acids to react with polyalkylene polyamines under conditions which produce ring closure such as the reaction of tetraethylene pentamine with stearic acid; waxes such as vegetable waxes and hydrocarbon waxes; organofunctional coupling agents which include silane and siloxane or titanate chelating agents having reactable or nonreactable organic moieties such as alkyls, amino alkyls, epoxy alkyls, acrylic alkyls, and the like; starches including hydrolyzed and derivatized starches and polymeric film forming materials such as epoxies, polyesters, polyolefins, polyurethanes, free radical polymerization vinyl polymers including homopolymers and copolymers such as polyvinyl acetate, polyvinyl acrylates, polyvinyl methacrylates, polyvinyl alcohol; elastomeric materials such as styrene butadiene copolymers, carboxylated polybutadiene and carboxylated styrene butadiene copolymers, polybutadiene and the like; aldehyde condensate polymers such as melamine formaldehyde, phenol formaldehyde, resorcinol formaldehyde and urea formaldehyde; emulsifiers and surfactants and the like and mixture of these materials. One example of a fluid chemical treatment with more than one carbonaceous material applied to siliceous fibers is U.S. Pat. No. 3,231,540 which is hereby incorporated by reference. Another example is that of U.S. Pat. No. 4,049,597 also hereby incorporated by reference.

The amount of the fluid chemical treatment with the carbonaceous material applied to the glass shapes is an effective amount which depends upon the amount of heat softenable, phase separable components of the glass shape and on the type of carbonaceous material. The amount of the fluid chemical treatment is that which provides the glass shapes with sufficient quantities of deposited carbonaceous material to reduce the tack bonding by being present on the surfaces of the glass shapes which are subjected to heat treatment for phase separation. Also the amount of the fluid chemical treatment applied to the glass shapes is sufficient to result in deposition of the carbonaceous material as a liquid, semisolid, or solid film coating, reaction product residue or particles depending on the type of carbonaceous material. The deposition is such that the carbonaceous material is present in one or more of the aforementioned forms on a substantial portion of the surfaces of the glass shapes. In the fluid chemical treatment, the moisture content should be controlled for the very high boron content glass shapes. The control is such that no more than limited amounts of boric acid are formed on the surface of the glass shapes through the interaction of the moisture with the boron-containing materials in the glass. In addition, moisture is controlled to limit volatilization of boron-containing materials from the surface of the glass shapes.

The deposited carbonaceous material is present during the heat treatment for phase separation. This presence need not be through the entire heat treatment cycle in order to reduce tack bonding, but the presence is through a substantial portion of the heat treatment. The substantial portion is such that the carbonaceous material may be totally removed during heat treatment as long as it was present for a majority of the time of the heat treatment. Further, it is believed without limiting the invention that the carbonaceous material, which is present, even if as decomposed carbon, may become associated with the heat softenable leachable components of the heat treated glass, and retard the tack bonding of glass shapes during heat treatment. The substantial portions of the surfaces of the glass shapes on which the one or more carbonaceous materials are deposited in various forms are such that during heat treatment, the chance of contact between a minority of portions of glass shapes without deposits is reduced. Generally, the amount of fluid chemical treatment with the carbonaceous material can be like those amounts of sizes, binders or coatings present on commercially available glass fibers. If this amount is too great, a more vigorous subsequent removal step can be utilized.

The fluid chemical treatment can be applied to glass shapes such as beads, flakes, platelets and particles by any method of contacting these materials or their glassy precursors with a fluid as known to those skilled in the art such as dip coating, spraying and the like. When the glass shapes are fibers being formed from a bushing, the fluid chemical treatment can be applied by contact with the fibers through roller, belt, pad, spray or direct applicator or the like. It is preferred in applying fluid chemical treatment to glass fibers that the treating composition has a mixture of carbonaceous materials to protect the glass fibers from interfilament abrasion in further processing steps.

If after the application of the fluid chemical treatment with the carbonaceous material to the glass shapes, an adequate deposit of carbonaceous material has not been formed, the treated glass shapes can be treated to develop adequate deposits on a substantial portion of the treated glass shapes. For example, the formation of solid deposits can vary from air drying to drying at elevated temperatures or treating in a reaction environment, i.e., temperature, pressure or radiant energy to produce the various forms of solid deposits, i.e., film, coating, residue or reaction products. These deposits would be substantially free of moisture for the aqueous chemical treatments and substantially free of liquids for the organic chemical treatments. The presence of too much liquid or water on the glass shapes could have an adverse affect when the glass shapes are heat treated for phase separation. Preferably, any deposit should contain less than around 20 weight percent moisture and most preferably less than around 10 weight percent moisture. The formation of the solid deposits can occur by any method known to those skilled in the art in developing solid deposits on distinct solid articles from a fluid treatment and in any type of art recognized apparatus. For instance, in forming glass fibers that are treated with an aqueous chemical treatment, the fibers are gathered into one or more strands and wound into a multi-layered package or chopped into small length chopped fibers. The winding of the one or more strands into a forming package can occur at speeds anywhere in the range of 2,000 to 20,000 feet per second. It is preferred that in producing these glass shapes, the amount of the aqueous chemical treatment with carbonaceous material is applied in such an amount that upon winding the glass fiber strand or strands into the forming package, the glass fibers are adequately dried to form a dried residue type of solid deposit of the carbonaceous material on a substantial portion of the surfaces of the glass fibers. In other cases, deposit formation could be accomplished by air drying for a sufficient period of time, or by drying at elevated temperatures for a sufficient period of time for removal of moisture or organic solvents or for conducting a chemical reaction of reactants in the chemical treatment to result in a carbonaceous material covering.

Distinct glass shapes such as beads, capillaries, tubes, chopped fibers or strands, chopped or continuous fiberous or strand mats or batts are treated directly for pore generation. Glass shapes such as continuous fibers and strands collected on multi-layered packages either forming or roving packages may be removed from the packages by cutting or rewinding onto larger diameter drums, or they can remain in the packages or pore generation. Preferably, the strands are cut from one or more multilayered packages by making one or more cuts through the layers in a lengthwise manner extending parallel to the lengthwise axis of the package. The length of the cut glass fibers can be varied by varying the diameter of the forming package during winding of the glass fibers or by rewinding the glass fibers from the forming package onto a smaller or larger diameter package. The many layers of glass fibers which are removed from the package can be laid flat on a supporting surface. The supporting surface can be a plate or tray or moving conveyor belt. Generally, the discrete lengths of glass fibers obtained by this approach can range from about 1 inch to around 25 inches. Any other method for removing the glass fibers from the multilayered package can be employed. For example, the fibers can be unwound from the package and disposed as chopped strand or continuous strand onto another supporting surface or holder or rotating drum. Preferably, the discrete lengths of glass fibers can range from about 0.25 inch (0.64 cm) to around 70 inches (180 cm) and most preferably up to around 25 inches (64 cm).

The chemically treated glass shapes with the deposit of the carbonaceous material are heat treated to phase separate the components which can be leached from silica. The heat treatment usually is conducted in an oven, or furnace, or on a heated drum for continuous fibers and strands at a temperature greater than the annealing temperature of the glass and less than the softening point temperature of the glass. The glass shapes can be water leached before they are acid leached, where the heat treatment, water leaching and acid leaching are conducted in accordance with the teachings of U.S. Pat. No. 3,843,341 hereby incorporated by reference. Some glass shapes with higher amounts of boron-containing material can have pores of sufficient dimensions generated by heat treatment for phase separation followed by water leaching alone. Other glass shapes having around 20 to less than 30 or 35 weight percent boron oxide or anhydride can have heat treatment for phase separation followed by water and/or acid leaching or merely acid leaching as described in U.S. Pat. Nos. 4,042,359; 2,106,744 and 3,485,687, all hereby incorporated by reference.

Porous glass shapes having pores generated from glass compositions with large amounts of water and/or acid leachables have a substantial amount of these leachable materials removed during leaching which usually results in satisfactory pores. The water and/or acid leachables refers to the materials, like boron-containing materials, in the glass other than silica that are leached by water or acids that do not leach silica directly, but that may leach silica gel or silica chemically associated with the phase separated non-silica materials. Porous glass shapes having a composition with an amount of water and/or acid leachable components of less than 30 and usually less than 20 weight percent, can have their pores enlarged to a desired mean pore diameter and pore volume or by alkali leaching or leaching with hydrofluoric or phosphoric acid. Alkali leaching and this type of acid leaching increases the size of generated pores through the removal of any residual boron-containing material, alkali metal and/or alkaline earth metal oxides and some siliceous material. Since this type of acid or alkali treatment removes some of the silica, the treatment must be carefully controlled to insure against excessive removal of the siliceous materials. This is particularly true when discrete glass fiberous lengths are desired.

An alkali leach to remove colloidal silica from the pores and some silica of the silica-rich fibers to yield porous fibers of discrete lengths involves contacting the fibers with an alkali solution generally equivalent to about 0.5 normal sodium hydroxide at ambient temperatures, preferably 25° C. for up to about 16 hours and preferably around 2 hours or less. The alkali solution may be more or less concentrated with a commensurate adjustment in the time of alkali treatment. Nonexclusive examples of bases equivalent to sodium hydroxide that can be used in alkali leaching include other alkali metal or alkaline earth metal hydroxides, mono-di-or triacid bases, and other inorganic and organic basic material equivalent to these in leaching ability. The alkali leach can enlarge the pores to the desired mean pore diameter and to the desired pore volume. Other alkali leaching or hydrofluoric acid leaching or phosphoric acid leaching operations for glass known in the art can be used. Between any of the leaching steps, it is preferred to wash the fibers with water.

During heat treatment at the conventional temperatures of about 400° C. (725° F.) to about 600° C. (1112° F.) some of the deposit having one or more carbonaceous materials is removed. The removal usually occurs through carbonization. As long as enough of the deposit is present during a majority of the duration of heat treatment, the benefits of the invention are realized. Preferably, some of the deposit remains after completion of the time for heat treatment. It has been found that the carbonaceous deposit on the heat treated glass shapes also protects the shapes from abrasion in the water, acid or alkali leaching steps. During the leaching steps, additional amounts of the carbonaceous deposits are released from the glass shapes.

After the completion of the one or more leaching steps, the porous glass shapes may still contain some of the carbonaceous deposits. the remaining deposits may be nothing more than a residue of carbon. Preferably, the amount of the deposit on the glass shapes was an effective LOI (loss on ignition) that some of the carbonaceous deposit remains after both heat treatment and the one or more leaching steps. The remaining deposit can range from a disintegrated film containing carbon to a recognizable film with pores.

FIG. 1 depicts a photograph of the deposit-glass interface of a heat treated, water leached, chemically treated glass fiber. The photograph was taken in a scanning electron microscope magnifying the interface 12,000 times. Reference numeral 10 indicates the remaining carbonaceous deposit after heat treatment and water leaching. Reference numeral 12 indicates the porous glass, where the dark areas do not necessarily indicate pores but only indicate distortions in the planar surface.

Figure 2:
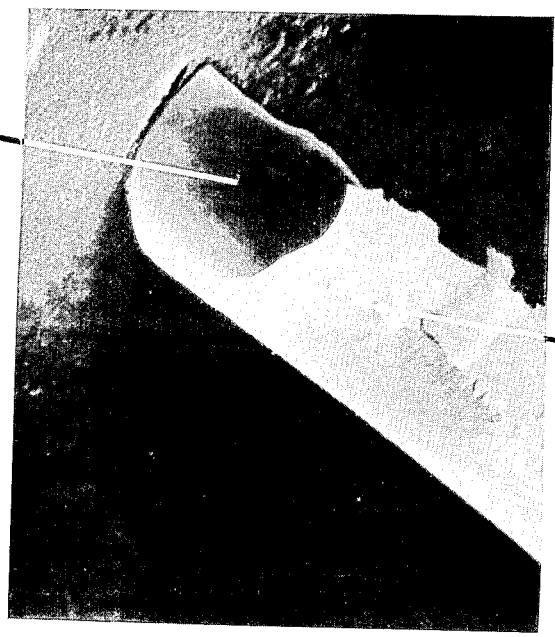
FIG. 2 is a photograph of the chemically treated porous silica-rich glass fiber from a scanning electron microscope where the carbonaceous deposit has been removed by heating in the electron beam.

FIG. 2 depicts a surface view of the heat treated, water leached, coated glass fibers magnified 600 times with the scanning electron microscope. Numeral 14 indicates the porous glass fiber, while numeral 16 indicates the carbonaceous deposit, which has been peeled back by the process of producing the magnified image by scanning electron microscopy. The process for both FIGS. 1 and 2 involved coating the specimens with gold in a conventional manner and placing the specimens in the scanning electron microscope.

Upon completion of acid leaching or alkali leaching, if used, the glass shapes are water washed. If the glass shapes have any residual carbonaceous deposit on the glass surface, the carbon is removed. The glass shapes may not have residual carbon if the carbon was removed by the completion of the heat treating step or in one of the leaching steps. If carbon or carbonaceous material is present in the glass shapes, it is removed by oxidation from the glass shapes, preferably at a temperature in the range of about 800° F. to about 1300° F. (427° C.–704° C.) for an effective period of time to remove the carbon or carbonaceous material, and most preferably around 1000° F. (538° C.) for a period of time of up to around two hours. In oxidizing any remnants of the carbonaceous deposit from porous glass shapes, the temperature of the oxidation treatment should be less than around 1093° C. (2000° F.) if shrinkage of the porous shape including large scale pore shrinkage and collapse is to be avoided. For the porous glass shapes that are porous glass fibers, the strength of the fibers, independently or in the form of a bundle of fibers, can be important in certain applications. In this case, the temperature of the oxidation treatment should be limited to less than 1300° F. (704° C.) to avoid too much degradation in the strength of the porous fibers. Also the time of the oxidation treatment depends on the amount of liquid chemical treatment originally applied. If larger than necessary amounts were applied, then longer times of oxidation may be required. The oxidizing environment is provided by air, oxygen, ozone or a mixture thereof or by the presence of oxygen yielding salts such as $KNO_3$, $KClO_3$ and the like. Preferably, the oxidizing environment is Provided by a constant flow of dry air around the glass shapes in the neat treating zone.

The heat treating zone can be any oven or furnace that accommodates the oxidizing environment and elevated temperature.

Figure 3:
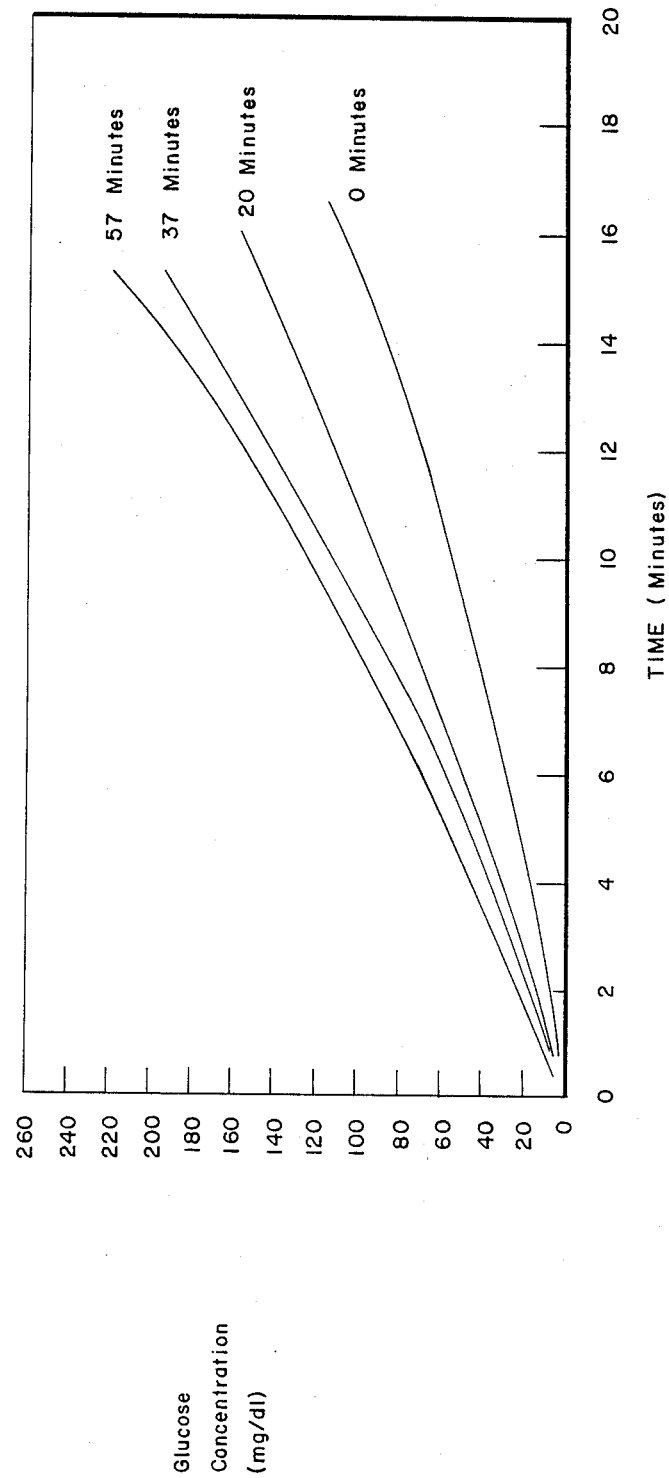
FIG. 3 is a graph of time as the independent variable versus glucose concentration to show the effect of decarbonization time on effectiveness of the pore size of the porous silica-rich glass fibers.

FIG. 3 shows the effect of removing the remnants of the carbonaceous material from the porous glass shapes to yield effective pores. Porous glass fiber samples were subjected to oxidation treatments for the indicated varying periods of time at 1000° F. (538° C.). The porous glass fiber samples had the same enzyme immobilized on the external and internal surfaces of the fiber samples in the same manner. All of the samples with immobilized enzyme were placed in contact with the same amount of starch. The conversion of starch to glucose was measured by the Somogy-Nelson method. The results graphed on FIG. 3 show higher conversions for longer periods of oxidation. It is believed without limiting the invention that this means that more pores were available for enzyme immobilization to give higher loadings of enzymes and a higher conversion. The higher availability of pores means more effective pores that were not blocked by any carbonaceous materials unassociated with the glass structure.

The porous glass shapes of the present invention are silica-rich with greater than around 75 and, preferably around 90 to 95, weight percent silica or, in the alternative around 90 or more weight percent silica and glass modifying material like zirconia oxide. The porous glass shapes should be essentially free of any carbon or carbonaceous material unassociated with the glass structure and generally has an amount of carbon or carbonaceous material of less than around 5 weight percent. The mean pore diameters of the porous shapes can be from around 10 to around 3,000 angstroms. The hollow porous glass fibers with distinct lengths can have a surface area including both external and internal surface areas of around 400 m²/gm or more. The pore volume of the porous shapes can be around 0.5 to about 1.5 cc/gm.

The porous glass shapes with effective pores can be utilized in many applications. The shapes can have various chemicals such as catalysts, enzymes and biomaterials such as antibodies and cells immobilized in or around the pores. Also, the shapes can be placed in reactors or containers for desalination of water or for performing chemical separations. In the case of enzyme immobilization, any immobilization technique known to those skilled in the art can be used where good enzyme loading in the pores is possible as shown in FIG. 3.

PREFERRED EMBODIMENT OF THE INVENTION

The glass forming, fiberizable, pore generating batch composition is formulated by back calculations to result in glass fiberous shapes that are heat treatable for phase separation into components of the water and/or acid leachable group and the alkali leachable group like alkali metal borosilicate glass compositions. The formulation also allows for removal of a substantial portion of the former group through water and acid leaching without the necessity of alkali leaching to achieve discrete lengths of glass fibers with sufficient pore diameters and volume.

The glass fiber forming batch most preferably provides fibers with a glass composition having about 54 weight percent $B_2O_3$, 8 weight percent $NaO_2$, and about 38 weight percent $SiO_2$. This glass composition is formed by melting the batch at about 2282° F. (1250° C.) for 2 hours and is formed into glass fibers at about 1610° F. (877° C.) by mechanical attenuation from a bushing. The fibers formed have a diameter in the range of about 3 microns to about 120 microns and, most preferably, about 10 microns to about 40 microns. Most preferably, the fibers are formed into hollow glass fibers with an outer diameter in the aforementioned range and an internal diameter to give a K factor in the range of up to around 0.9. The K factor is the ratio of inner diameter to outer diameter. The air flow to the hollow fiber bushing is satisfactory to result in the desired K factor and for a ten tip bushing is usually in the range of greater than 0 to about 0.5 cfm (cubic feet per minute). The glass fibers are sized with an aqueous chemical treating composition preferably having a film forming polymer like epoxy resin, which is water soluble, dispersible or emulsifiable, and water soluble lubricant like Cation-X ® lubricant and a compatible organosilane coupling agent like an epoxy silane. The fibers are gathered into one or more strands and wound into a cylindrical forming package.

A plurality of undried forming packages are cut along their longitudinal axes so that all of the layers of the glass fibers can be removed from the package. These fibers are laid straight on trays in a nearly parallel alignment, where the fibers usually have a discrete length of about 25 inches (63.5 cm).

The fibers are heat treated at a temperature in the range of about 420° C. to about 600° C. for a period of time from about 10 minutes to several days. Longer times require lower temperatures while shorter times require higher temperatures in these range. Most preferably, the fibers are heat treated at 540° C. for 6 hours to phase separate the water and acid leachable material in the glass fibers. For the glass fibers with higher amounts of boron-containing materials, lower heat treating temperatures also may be used to assist in decreasing any sticking together of the glass fibers, while the presence of a protective size allows utilization of higher heat treating temperatures. Afterwards, the fibers are cooled to ambient temperatures.

The glass fibers are leached, with water followed by an acid leach. In the water leach, the glass fibers are immersed in a water bath for a sufficient period of time, at a sufficient temperature to remove a substantial amount, if not all, of the water soluble boron-containing compounds in the glass fibers. The glass fibers are submerged in the water when the water is cool and the temperature of the water is increased to an elevated temperature preferably around 80° to 100° C., most preferably around 95° C., for 1 to about 24 hours, preferably 3 hours. It is preferred that the water leaching step be performed in a vessel that accommodates agitation which is performed during the water leaching step. If the temperature of the water bath falls below 80° C., there is less thorough leaching and there must be a substantial increase in the leaching times. The time of leaching depends on the temperature of the bath and size of the fiber being treated. In order to keep the fibers aligned during the leaching process, they are immobilized usually by placing a rod perpendicular to the long axis of the fibers to hold them stationary. The volume ratio of water to glass fibers in the leaching bath can be about 2 to 8 volumes of water to one volume of glass fibers. Low water to glass fiber volume ratios slow the leaching process while higher volume ratios serve no particular advantage.

After water leaching, the glass fibers are removed from the water solution. The glass fibers are then acid leached, with agitation, in a dilute acid solution, such as 0.1 to about 3 Normal, preferably, about 0.1 to 0.5 Normal hydrochloric acid, at temperatures around 80° C. to 100° C., preferably 90° C., for about 0.5 to about 8 hours, preferably about 2 to about 4 hours. Generally, the dilute acid solution removes any remaining traces of boron, alkali metal oxides and alkali metal borates so that the pores are unplugged of these materials. Nonexclusive examples of other suitable dilute solutions of acids include sulphuric and nitric acid, or organic acids such as oxalic acid. The volume ratio of acid to glass fibers in the acid leaching step can be about 1 to about 8 volumes of acid to one volume of glass fibers which will vary somewhat with the normality of the acid. The glass fibers are removed from the acid leaching solution, water washed to a pH of around 5.5 to neutral in the wash water after which the fibers are dried, preferably in air drying at around 100° C. for around one hour to about 24 hours.

The porous glass fibers are subjected to air oxidation to remove any carbonaceous residue in the pores that may result from the deposit of sizing composition being present on the glass fibers during heat treatment. The temperature of oxidation is that sufficient to oxidize carbon in the presence of an adequate amount of flowing dry reconstituted air and it is most preferably at around 1000° F. (537° C) or higher for about 20 minutes up to about 2 hours. The oxidation temperature should not be of such magnitude that the glass revitrifies and closes the pores.

The invention is further elucidated but not limited by the following example.

A batch composition calculated to yield the desired oxide amounts of the most preferred glass composition was melted in platinum crucibles at 2282° F. (1250° C.) for 1 hour with occasional stirring. A 10 nozzle glass fiber bushing which was electrically heated, was charged with melted glass forming batch and conditioned at 2000° F. (1093° C.) for 1 hour to remove seeds from the melt. The current to the bushing was adjusted and the tip plate was then set for a 1600° F. (871° C.) temperature and the melt thermocouple read 1687° F. (919° C.). Glass fibers were formed by mechanical attenuation onto an 8 inch collet that was rotated at 295 RPM to form 70 micron solid fibers. During their formation, the fibers were treated with an aqueous chemical treatment of U.S. Pat. No. 4,049,597, hereby incorporated herein, without any hydrogenated corn oil, and without any anionic and cationic emulsifiers and with the addition of magnesium chloride as an antistatic agent. The fibers were sliced off of the resulting package in multiple layers of 25" long fibers × 70 micron OD. The fibers were cut from the collet and laid out in a heat treating furnace for phase separation. During heat treatment, the binder began to oxidize, however, some of the carbon was entrapped in the fiber surfaces, probably in high boron areas. After heat treatment, the fiber was grey to black in appearance. The color is dependent on fiber OD and binder pickup.

The fibers were leached for 6 hours at 95° C. in distilled water and at 95° C. in 0.2 N HCl. During leaching, some carbon was released from the glass forming a carbon film on the bath surface. These fibers were water washed until neutral, then dried overnight at 110° C. on flowing dry air. One sample was not heat treated while 3 samples were heat treated in air at 1000° F. for 20 minutes, 37 minutes and 57 minutes, respectively. Glucoamylose was immobilized on each fiber set by previously described methods and the loading was measured. The graph of FIG. 3 shows the effect of heat treatment time to remove carbon on enzyme activity and loading. Heat treatment in air for 2 hours at 1000° F. was sufficient to remove all residual carbon.

I claim:

1. Method of producing a plurality of distinct, silica-rich, glass shapes with effective pores having greater than around 75 weight percent silica and being essentially free of remnants of carbonaceous material, comprising:
   a. forming distinct glass shapes from a heat treatable, leachable glass composition having one or more phase separable materials that lower the melting point of the glass,
   b. treating the distinct glass shapes so formed with a fluid chemical treatment having one or more carbonaceous materials to deposit the carbonaceous materials on a substantial portion of the surfaces of the distinct glass shapes,
   c. heat treating the plurality of chemically treated glass shapes at a temperature in the range of about 400° C. to about 600° C. to phase-separate at least some of the phase separable materials,
   d. leaching the phase-separated glass shapes to remove a substantial amount of the phase-separated, leachable materials to form porous, silica-rich glass shapes,
   e. removing remnants of the carbonaceous material in an on the porous, silica-rich, glass shapes so that the shapes are essentially free of carbon.

2. Method of claim 1, wherein the glass shapes are selected from the group consisting of particles, platelets, flakes, beads, fibers, tubes, capillaries and hollow fibers.

3. Method of claim 1, wherein the one or more carbonaceous materials is selected from the group consisting of one or more water soluble, emulsifiable or dispersible polymeric film forming material, lubricants, waxes, coupling agents, starches, emulsifiers, surfactants and mixtures thereof.

4. Method of claim 1, wherein the removal of residual carbon through oxidation is at a temperature of about 800° F. to less than around 2,000° F. (1093° C.) for a period of time of up to around 2 hours to avoid shrinkage of the porous shapes.

5. Method of claim 1, wherein the materials that are leached from the phase-separated glass include a boron-rich group having boron oxides, alkali metal oxides, and alkali metal borates.

6. Method of claim 1, wherein the heat treating is conducted for a period of time of around 10 minutes to around 64 hours.

7. Method of claim 1, wherein the distinct glass shapes have a heat treatable and leachable glass composition of boron-containing material in an amount in the range of around 20 to around 60 weight percent, and alkali metal oxide in an amount in the range of around 4 to around 20 weight percent and always having an amount of siliceous material of at least around 25 weight percent, where the amount of siliceous material can be in the range of about 25 to around 85 weight percent of the glass composition.

8. Method of claim 1, wherein the chemically treated distinct shapes have a solid deposit of the carbonaceous material formed on them as a deposit selected from the group consisting of: film, coating, reaction product residue, particles, and mixtures thereof.

9. Method of claim 1, wherein the glass shapes are formed from glassy precursors that are treated with the fluid chemical treatment and formed from the heat treatable, leachable glass composition.

10. Method of claim 1, wherein the leaching is performed with a leaching agent selected from the group consisting of water, or acid or a combination thereof where the combined leaching is performed by water leaching followed by acid leaching.

11. Method of claim 10, wherein the leaching includes alkali leaching after the water and/or acid leaching.

12. Method of claim 1, wherein the removal of the remnants of the carbonaceous material includes removal of residual carbon through oxidizing at an elevated temperature in the range of about 400° C. to less than around 1300° C. for an effective period of time to remove the carbon.

13. Method of claim 1, wherein heat treating the glass shapes carbonizes some of the carbonaceous material.

14. Method of claim 1, wherein leaching the phase separated glass shapes removes some of the carbonaceous material.

15. Method of claim 1, wherein the porous silica-rich, glass shapes have around 90 to 95 weight percent silica.

16. Method of claim 1, wherein the forming of distinct glass shapes with a heat treatable, leachable glass composition involves a composition having a silica-rich group comprising silica and oxides of glass modifiers selected from the group consisting of aluminum, zirconium and titanium.

17. Method of claim 16, wherein the forming of the distinct glass shapes utilizes the heat-treatable, leachable glass composition having zirconium and the porous, silica-rich glass shapes have an amount of silica of around 90 or more weight percent and have present a zirconia oxide.

18. Method of claim 1, wherein removing the remnants of the carbonaceous material results in less than around 5 weight percent carbon in the porous, silica-rich glass shapes.

* * * * *